(12) United States Patent
Tachon et al.

(10) Patent No.: US 11,806,424 B2
(45) Date of Patent: Nov. 7, 2023

(54) PORE HIDING COSMETIC COMPOSITION COMPRISING A PLATE TYPE FILLER, A SILICON ELASTOMER AND AN OIL ABSORBING FILLER

(71) Applicant: L'OREAL, Paris (FR)

(72) Inventors: Romain Tachon, Tokyo (JP); Momoko Shimizu, Kawasaki (JP)

(73) Assignee: L'OREAL, Paris (FR)

( * ) Notice: Subject to any disclaimer, the term of this patent is extended or adjusted under 35 U.S.C. 154(b) by 191 days.

(21) Appl. No.: 17/002,941

(22) Filed: Aug. 26, 2020

(65) Prior Publication Data

US 2020/0390683 A1 Dec. 17, 2020

Related U.S. Application Data

(62) Division of application No. 14/408,719, filed as application No. PCT/JP2012/066471 on Jun. 21, 2012, now abandoned.

(51) Int. Cl.
| | | |
|---|---|---|
| *A61K 8/891* | (2006.01) | |
| *A61K 8/37* | (2006.01) | |
| *A61Q 1/00* | (2006.01) | |
| *A61K 8/25* | (2006.01) | |
| *A61K 8/02* | (2006.01) | |
| *A61K 8/19* | (2006.01) | |
| *A61Q 1/02* | (2006.01) | |
| *A61K 8/893* | (2006.01) | |
| *A61K 8/58* | (2006.01) | |
| *A61K 8/06* | (2006.01) | |
| *A61K 8/29* | (2006.01) | |

(52) U.S. Cl.
CPC ............ *A61K 8/891* (2013.01); *A61K 8/0254* (2013.01); *A61K 8/06* (2013.01); *A61K 8/19* (2013.01); *A61K 8/25* (2013.01); *A61K 8/29* (2013.01); *A61K 8/37* (2013.01); *A61K 8/585* (2013.01); *A61K 8/893* (2013.01); *A61Q 1/00* (2013.01); *A61Q 1/02* (2013.01); *A61K 2800/412* (2013.01)

(58) Field of Classification Search
None
See application file for complete search history.

(56) References Cited

U.S. PATENT DOCUMENTS

| | | |
|---|---|---|
| 5,538,793 A | 7/1996 | Inokuchi et al. |
| 5,750,723 A | 5/1998 | Eldin et al. |
| 5,847,156 A | 12/1998 | Eldin et al. |
| 6,048,918 A | 4/2000 | Eldin et al. |
| 6,649,173 B1 | 11/2003 | Arnaud et al. |
| 7,470,725 B2 | 12/2008 | Schwertfeger et al. |
| 2004/0175338 A1 | 9/2004 | Filippi et al. |
| 2004/0202627 A1 | 10/2004 | Kuroda et al. |
| 2005/0061205 A1 | 3/2005 | Kobayashi et al. |
| 2005/0079190 A1 | 4/2005 | Polonka |
| 2005/0163730 A1 | 7/2005 | Rosevear et al. |
| 2006/0293431 A1 | 12/2006 | Kani et al. |
| 2009/0081316 A1 | 3/2009 | Wahl et al. |
| 2012/0084780 A1 | 4/2012 | Pasternak |

FOREIGN PATENT DOCUMENTS

| | | |
|---|---|---|
| CN | 1863499 A | 11/2006 |
| EP | 0242219 A2 | 10/1987 |
| EP | 0295886 A2 | 12/1988 |
| EP | 0542669 A1 | 5/1993 |
| EP | 0765656 A1 | 4/1997 |
| EP | 0787730 A1 | 8/1997 |
| EP | 0787731 A2 | 8/1997 |
| EP | 0847752 A1 | 6/1998 |
| EP | 1481659 A1 | 12/2004 |
| EP | 1870078 A2 | 12/2007 |
| EP | 2292207 A1 | 3/2011 |
| EP | 2502966 A1 | 9/2012 |
| FR | 2944701 A1 | 10/2010 |
| JP | 48-035046 A | 5/1973 |
| JP | 61-194009 A | 8/1986 |
| JP | 07-206639 A | 8/1995 |
| JP | H08-73319 A | 3/1996 |
| JP | 2002-154929 A | 5/2002 |
| JP | 2002-212032 A | 7/2002 |
| JP | 2004-210655 A | 7/2004 |

(Continued)

OTHER PUBLICATIONS

Dow Corning VM-2270 Aerogel Fine Particles (published Apr. 1, 2009), (Year: 2009).*
International Search Report and Written Opinion for PCT/JP2012/066471.
"Formulation Guidelines for formulating Effect Pigments in Lipstick and Lip Gloss Applications," Eckart Effect Pigments, XP055067270, Jan. 1, 2009, pp. 1-5, Retrieved from the Internet: http://www.eckart.de/fileadmin/ECKART/downloads/formulations/cosmetics/Formulation_guidelines_for_formulating_effect_pigments_in_lipstick_and_lip_gloss_applications_update_Sept_09.d.pdf [retrieved on Jun. 19, 2013].
"Marzipan Souffle: Make up Base, Sebum Control Formulation 00924," Dow Coming, XP055055418, Nov. 18, 2006, pp. 1-2, Retrieved from the Internet: http://www1.dowcorning.com/content/publishedlit/FORMUL_00924.pdf [retrieved on Mar. 6, 2013].

(Continued)

*Primary Examiner* — David J Blanchard
*Assistant Examiner* — Sarah J Chickos
(74) *Attorney, Agent, or Firm* — THE MARBURY LAW GROUP, PLLC

(57) ABSTRACT

The invention relates to a cosmetic composition, in particular in the form of a liquid cosmetic composition, comprising in a physiological medium (i) at least a plate type filler with refractive index>1.6 and having a particle size between 1 µm and 20 µm, preferably between 1 µm and 15 µm, (ii) at least a silicon elastomer, preferably a non-emulsifying silicon elastomer, and (iii) at least a filler having an oil absorption capacity greater than or equal to 1 ml/g. The composition is preferably used as a skin care or make-up base or primer intended to decrease the visibility of skin imperfections, in particular the pores and make the pore hiding effect long lasting.

14 Claims, No Drawings

(56) References Cited

FOREIGN PATENT DOCUMENTS

| JP | 2009-137900 | A | 6/2009 |
|---|---|---|---|
| JP | 2010-513368 | A | 4/2010 |
| JP | 2010-521399 | A | 6/2010 |
| WO | 96/08537 | A1 | 3/1996 |
| WO | 2008/077728 | A2 | 7/2008 |
| WO | 2008/115812 | A2 | 9/2008 |
| WO | 2011/082019 | A1 | 7/2011 |
| WO | 2012/084780 | A2 | 6/2012 |

OTHER PUBLICATIONS

"Oil absorbing facial serum—"pure pearl"", XP055068120, Jan. 1, 2007, Retrieved from the Internet: http://www.eckart.net/fileadmin/ECKART/downloads/formulations/cosmetics/skincare/SC0368A_Oil_Absorbing_Facial_Serum_Pure_Pearl.pdf [retrieved on May 25, 2013].

English language abstract for JP 61-194009 (Aug. 28, 1986).

Japanese Office Action for copending JP Application No. 2014-560579, dated Feb. 8, 2016.

Chinese Office Action for CN Application No. 201280074039.7, dated Nov. 14, 2016 (translation attached).

Japanese Office Action for JP Application No. 2014-560579, dated Nov. 7, 2016 (translation attached).

Cosmetics (Make-up base), Product Name "Tsurutsuru Make-up Base III" (Selling agency: HABA Laboratories Inc.), Mintel: GNDP-GLOBAL New Products Database (https://portal.mintel.com/portal/), Launching date (database registered date): (Apr. 2012), 2 pages.

Toshihiko Funabashi et al., Development and Application of high purity hexagonal boron nitride (h-BN) powder, Kawasaki Steel Technical Report 24 (1992) 2, pp. 135 to 141.

Silicone compound powder "KSP-100 Series", Shin-Etsu Chemical Co., Ltd., Fragrance Journal 2000-2, Concise explanation of relevance 4 Yoshiki Nakajima (2007), Compounding agent of AGC, pp. 73 to 75.

Yoshiki Nakajima (2007), Compounding agent of AGC-sitech, JET vol. 55, No. 9, p. 214.

Japanese Office Action for Application No. 2014-560579 dated Jul. 14, 2017, Partial Translation.

European Office Action for counterpart EP Application No. 12738234.9-1114, dated Dec. 18, 2018.

Evonik Industries, "Aerosil®—Fumed Silica Technical Overview," Dec. 31, 2015.

Non-Final Office Action for copending U.S. Appl. No. 14/408,719, dated Nov. 19, 2015.

Final Office Action for copending U.S. Appl. No. 14/408,719, dated Jul. 20, 2016.

Non-Final Office Action for copending U.S. Appl. No. 14/408,719, dated Aug. 7, 2018.

Final Office Action for copending U.S. Appl. No. 14/408,719, dated Apr. 8, 2019.

Non-Final Office Action for copending U.S. Appl. No. 14/408,719, dated Oct. 25, 2019.

Final Office Action for copending U.S. Appl. No. 14/408,719, dated Apr. 30, 2020.

Non-Final Office Action for copending U.S. Appl. No. 14/408,719, dated Apr. 21, 2017.

Final Office Action for copending U.S. Appl. No. 14/408,719, dated Nov. 1, 2017.

\* cited by examiner

PORE HIDING COSMETIC COMPOSITION COMPRISING A PLATE TYPE FILLER, A SILICON ELASTOMER AND AN OIL ABSORBING FILLER

CROSS REFERENCE TO RELATED APPLICATIONS

This is a Divisional of U.S. application Ser. No. 14/408,719, filed on Dec. 17, 2014, which is a National Stage Application of PCT/JP2012/066471, filed internationally on Jun. 21, 2012, both of which are incorporated by reference herein in their entireties.

TECHNICAL FIELD

This invention is related to a cosmetic composition, in particular in a liquid or fluid form, which includes an association of plate type fillers with high refractive index, silicon elastomers and oil absorbing particles. This cosmetic composition allows decreasing the visibility of pores once applied to on the skin. It also makes the pore hiding effect last during the day. By 'liquid' composition according to the invention, we mean liquid or fluid composition, by opposition to solid composition whose high hardness doesn't permit the composition to flow under its own weight.

BACKGROUND ART

Imperfections of the skin are visible because of the contrast between bright as such as skin ridges and dark areas such as skin pores. Light scattering can decrease this brightness gap and may be achieved by mat and haze effect. A good balance between filler oil absorption capacity and non-volatile oil content provides mat effect. Introduction of fillers with light scattering properties provides haze effect.

However, particles such as pigments which have strong light scattering and absorption should be avoided as they tend to accumulate inside the pores and enhance their visibility. As a conclusion, a fluid formula for pore hiding should contain fillers with strong oil absorption capacity, fillers with light scattering properties and preferably low amount of pigments.

Usually, sebum secretion during the day tends to alter optical effects achieved just after application of cosmetic composition on the skin.

It remains a need for having a cosmetic composition having pore hiding effect and keeping this effect during the day.

So far, fluid pore hiding makeup products mainly consist of water-in-oil emulsion including silicon elastomers and/or spherical fillers and/or plate fillers such as barium sulfate, composite materials, small pearls. US2009081316 from Momentive describes the association of silicon elastomer and boron nitride. US2005163730 from Unilever describes the association of silicon elastomer, ZnO nanopigment and plate type filler such as $TiO_2$ coated mica or bismuth oxychloride.

DISCLOSURE OF INVENTION

To the knowledge of the Applicant, there is none prior pore hiding fluid composition having association of (i) plate type fillers with medium to high refractive index (RI>1.6 and preferably <2.2) providing good coverage and light scattering, (ii) silicon elastomer to thicken the composition and enhance the pore hiding effect, and (iii) fillers having strong oil absorption to give haze and mat effect.

The invention concerns a cosmetic composition, in particular in the form of a liquid cosmetic composition, comprising in a physiological medium:
  (i) at least a plate type filler with refractive index>1.6 and having a particle size between 1 µm and 20 µm, preferably between 1 µm and 15 µm,
  (ii) at least a silicon elastomer, preferably a non-emulsifying silicon elastomer, and
  (iii) at least a filler having an oil absorption capacity greater than or equal to 1 ml/g.

In a particular embodiment, the composition of the invention is a base or a primer, in particular a skin care or a make-up base or primer.

The composition may comprise from 0 to 5% of dyestuffs by total weight of the composition.

In a preferred embodiment, the plate type filler has a refractive index 1.6<RI2.2.

In a particular embodiment, a cosmetic composition according to the invention comprises from 0 to 3% of dyestuffs by total weight of the composition.

The invention also concerns a cosmetic process comprising a step of applying at least one layer of the cosmetic composition according to the invention onto the skin, in particular the skin of the face.

In a particular embodiment, the cosmetic composition is applied as a base or a primer under a skin care product or a make-up product.

The cosmetic composition according to the invention is particularly intended to decrease the visibility of skin imperfections, in particular the pores and make the pore hiding effect long lasting.

BEST MODE FOR CARRYING OUT THE INVENTION

Plate Type Filler with High Refractive Index

The composition according to the invention comprises a least a plate type filler with high refractive index (RI>1.6) and particle size between 1 µm and 15 µm.

In particular the plate type filler has refractive index comprised between 1.6 and 2.2 and a particle size between 1 µm and 15 µm.

The particle size are expressed as the mean volume diameter (D[0.5]).

In particular, the said plate type filler is chosen from boron nitride, barium sulfate, bismuth oxychloride, alumina and composite powders based on titanium oxide and substrate like talc, mica, barium sulfate, boron nitride, bismuth oxychloride, alumina, and mixtures thereof.

In a particular embodiment, the plate type filler is a boron nitride.

In a preferred embodiment, the plate type filler is a boron nitride having a particle size between 1 µm and 10 µm, and in particular between 1 and 6 µm.

As examples of commercial products of boron nitride, we may use the following products: PUHP3008 from Saint Gobains Ceramics (mean particle size 6 µm), the PUHP1030L from Saint Gobain Ceramics (mean particle size 3 µm), the Softouch BN CC6058 powder from Momentive Performance Materials (mean particle size 5-15 µm), or mixtures thereof.

The plate type filler is present in the composition of the invention in an amount ranging from 0.5 to 20%, preferably from 1 to 10% and more preferably from 2 to 5% by weight of the total weight of the composition.

Silicon Elastomers (Organopolysiloxane Elastomer)

The composition according to the invention also comprises at least a silicon elastomer.

In a preferred embodiment, the composition comprises a non-emulsifying silicon elastomer.

The non-emulsifying silicon elastomer may be in form of a gel or a powder.

The 'organopolysiloxane elastomer' or 'silicon elastomer' makes it possible to thicken the composition and to improve the application properties thereof. It provides a very soft and mattifying feel after application, which is especially advantageous for an application to the skin. This elastomer is either a gel or a soft powder.

The expression "organopolysiloxane elastomer" or "silicone elastomer" means a flexible, deformable organopolysiloxane having viscoelastic properties and especially the consistency of a sponge or a flexible sphere. Its modulus of elasticity is such that this material withstands deformation and has limited stretchability and contractability. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of a dimethylpolysiloxane containing dimethylvinylsiloxy end groups and of methylhydrogenpolysiloxane containing trimethylsiloxy end groups, in the presence of a platinum catalyst.

Compound (A) is the base reagent for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, especially so as to be miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) may thus be chosen from methylhydrogenpolysiloxanes containing trimethylsiloxy end groups, dimethylsiloxane-methythydrosiloxane copolymers containing trimethylsiloxy end groups, and dimethylsiloxane-methylhydrosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups may be located in any position of the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) may be chosen from methylvinylpolysiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl-(3,3,3-trifluoropropyl)polysiloxanes containing dimethylvinylsiloxy end groups, and dimethylsiloxane-methyl(3,3,3-trifluoropropyl)siloxane copolymers containing dimethylvinylsiloxy end groups.

In particular, the organopolysiloxane elastomer may be obtained by reaction of dimethylpolysiloxane containing dimethylvinylsiloxy end groups and of methylhydrogenpolysiloxane containing trimethylsiloxy end groups, in the presence of a platinum catalyst.

Advantageously, the sum of the number of ethylenic groups per molecule in compound (B) and of the number of hydrogen atoms bonded to silicon atoms per molecule in compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units. Thus, according to one particular embodiment of the invention, the composition comprises an organopolysiloxane elastomer that is free of polyoxyalkylene units and polyglyceryl units.

Non-emulsifying elastomers are especially described in patents EP 242 219, EP 285 886 and EP 765 656 and in patent application JP-A-61-194 009.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC 9040 and DC 9041 by the company Dow Corning, and SFE 839 by the company General Electric.

Spherical non-emulsifying elastomers that may be used include those sold under the names DC 9040, DC 9041, DC 9509, DC 9505 and DC 9506 by the company Dow Corning.

In an embodiment, the organopolysiloxane elastomer particles are conveyed in the form of a gel formed from an elastomeric organopolysiloxane included in at least one hydrocarbon-based oil and/or one silicone oil. In these gels, the organopolysiloxane particles are often non-spherical particles.

As preferred non-emulsifying silicone elastomer in gel form, we may cite the INCI Name products Dimethicone crosspolymers such as DC9041, DC9045 from Dow Corning.

In another embodiment, the organopolysiloxane elastomer particles are conveyed in the form of a powder.

As preferred non-emulsifying silicone elastomer in powder form, we may cite the INCI Name products Dimethicone/Vinyldimethicone crosspolymer such as the DC9506 and DC9701 from Dow Corning and KSG6 from Shin Etsu.

In another embodiment, the composition of the invention comprises at least one silicone elastomer powder coated with a silicone resin. The silicone elastomer powder is spherical and may be obtained especially via the processes for synthesizing non-emulsifying elastomers described above. The silicone elastomer powder is coated with silicone resin.

According to one preferred embodiment, the silicone resin may be a silsesquioxane resin, as described, for example, in patent U.S. Pat. No. 5,538,793, the content of which is incorporated herein by way of reference. Such elastomer powders coated with, silicone resin are especially sold under the names KSP-100, KSP-101, KSP-102, KSP-103, KSP-104 and KSP-105 by the company Shin-Etsu. Such powders correspond to the INCI name dimethicone silsesquioxane crosspolymer, and in particular vinyl dimethicone/methicone silsesquioxane crosspolymer. As a preferred elastomer powder coated with silicone resin, we may use KSP100.

The silicone elastomer particles may have a hardness of less than or equal to 80 (especially ranging from 5 to 80) and preferably less than or equal to 65 (especially ranging from 5 to 65). The JIS-A hardness is measured according to the method JIS K 6301 (1995) established by the Japanese Industrial Standards Committee.

In particular, the silicone elastomer particles may have a mean size ranging from 0.1 to 500 μm, preferably from 3 to 200 μm and better still from 10 to 20 μm. These particles may be of spherical, flat or amorphous shape, and preferably of spherical shape.

This organopolysiloxane elastomer or silicon elastomer is present in the composition generally in a content ranging from 1% to 30% by weight of active material (=dry matter) and preferably from 2% to 10% by weight relative to the total weight of said composition.

Fillers with Oil Absorption Capacity Greater than or Equal to 100 ml/100 g

The composition according to the invention comprises also a filler having an oil absorption capacity greater than or equal to 100 ml/100 g, ie greater than or equal to 1 ml/g. The said filler according to the invention has capacity for absorbing and/or adsorbing an oil or a liquid fatty substance, for instance sebum (from the skin).

This oil-absorbing filler may also advantageously have a BET specific surface area of greater than or equal to 300 $m^2/g$, preferably greater than 500 $m^2/g$ and preferentially greater than 600 $m^2/g$, and especially less than 1500 $m^2/g$.

The BET specific surface area is determined according to the BET (Brunauer-Emmet-Teller) method described in the Journal of the American Chemical Society, vol. 60, page 309, February 1938 and corresponding to the international standard ISO 5794/1 (appendix D). The BET specific surface area corresponds to the total specific surface area (thus including micropores) of the powder.

The filler under consideration according to the invention is thus characterized in that it has an oil uptake of greater than or equal to 1 ml/g, preferably greater than or equal 1.5 ml/g, especially ranging from 1.5 ml/g to 20 ml/g, or even ranging from 1.5 ml/g to 15 ml/g. It preferably has an oil uptake of greater than or equal to 2 ml/g, especially ranging from 2 ml/g to 20 ml/g, or even ranging from 2 ml/g to 15 ml/g.

This oil uptake, which corresponds to the amount of oil absorbed and/or adsorbed by the filler, may be characterized by measuring the wet point according to the method described below.

Method for Measuring the Oil Uptake of a Filler

The oil uptake of a powder is measured according to the method for determining the oil uptake of a powder described in standard NF T 30-022. It corresponds to the amount of oil adsorbed onto the available surface of the filler, by measuring the wet point.

An amount m (in grams) of powder of between about 0.5 g and 5 g (the amount depends on the density of the powder) is placed on a glass plate and isononyl isononanoate is then added dropwise.

After addition of 4 to 5 drops of isononyl isononanoate, the isononyl isononanoate is incorporated into the filler using a spatula, and addition of the isononyl isononanoate is continued until a conglomerate of isononyl isononanoate and powder has formed. At this point, the isononyl isononanoate is added one drop at a time and the mixture is then triturated with the spatula. The addition of isononyl isononanoate is stopped when a firm, smooth paste is obtained. This paste must be able to be spread on the glass plate without cracking or forming lumps. The volume Vs (expressed in ml) of isononyl isononanoate used is then noted.

The oil uptake corresponds to the ratio Vs/m.

The oil-uptake filler under consideration according to the invention may be of organic or inorganic nature.

The filler having oil absorption capacity greater than or equal to 1 ml/g may be chosen more particularly from silicas, silica silylates (in particular hydrophobic silica aerogel particles), polyamide (in particular Nylon-6) powders, powders of acrylic polymers, especially of polymethyl methacrylate, of polymethyl methacrylate/ethylene glycol dimethacrylate, of polyallyl methacrylate/ethylene glycol dimethacrylate or of ethylene glycol dimethacrylate/lauryl methacrylate copolymer; perlites; magnesium carbonate, and mixtures thereof.

A person skilled in the art will select among the above-mentioned materials fillers with an oil uptake of greater than or equal to 1 ml/g, preferably greater than or equal to 1.5 ml/g and preferably greater than to or equal to 2 ml/g, which are in this respect suitable for use in the invention.

Advantageously, the oil-absorbing powder may be a powder coated with a hydrophobic treatment agent.

The hydrophobic treatment agent may be chosen especially from fatty acids such as stearic acid; metal soaps such as aluminium dimyristate, the aluminium salt of hydrogenated tallow glutamate; amino acids; N-acylamino acids or salts thereof lecithin, isopropyl triisostearyl titanate, mineral waxes, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds mentioned previously especially denotes an alkyl group containing from 1 to 30 carbon atoms and preferably containing from 5 to 16 carbon atoms.

Examples of fillers in accordance with the invention, i.e. fillers with an oil uptake of greater than or equal to 1 ml/g, preferably greater than or equal to 1.5 ml/g, are described below, with their oil uptake value measured according to the protocol described previously.

Silica powders that may be mentioned include:
porous silica microspheres, especially those sold under the names Sunsphere® H53 and Sunsphere® H33 (oil uptake equal to 3.70 ml/g) by the company Asahi Glass; MSS-500-3H by the company Kobo;
polydimethylsiloxane-coated amorphous silica microspheres, especially those sold under the name SA Sunsphere® H33 (oil uptake equal to 2.43 ml/g),
silica silylate powders, especially the hydrophobic silica aerogel particles sold under the name Dow Corning VM-2270 Aerogel Fine Particles by the company Dow Corning (oil uptake equal to 10.40 ml/g),
amorphous hollow silica particles, especially those sold under the name Silica Shells by the company Kobo (oil uptake equal to 5.50 ml/g), and
precipitated silica powders surface-treated with a mineral wax, such as precipitated silica treated with a polyethylene wax, and especially those sold under the name Acematt OR 412 by the company Evonik-Degussa (oil uptake equal to 3.98 ml/g).

Acrylic polymer powders that may be mentioned include:
porous polymethyl methacrylate (INCI name methyl methacrylate crosspolymer) such as the spheres sold under the name Covabead LH85 by the company Sensient,
porous polymethyl methacrylate/ethylene glycol dimethacrylate spheres sold under the name Microsponge 5640 by the company Cardinal Health Technologies (oil uptake equal to 1.55 ml/g), and
ethylene glycol dimethacrylate/lauryl methacrylate copolymer powders, especially those sold under the name Polytrap® 6603 from the company Dow Corning (oil uptake equal to 6.56 ml/g).

Polyamide powders that may be mentioned include:
nylon-6 powder, especially the product sold under the name Pomp610 by the company UBE Industries (oil uptake equal to 2.02 ml/g).

A perlite powder that may especially be mentioned is the product sold under the name Optimat 1430 OR by the company World Minerals (oil uptake equal to 2.4 ml/g).

A magnesium carbonate powder that may especially be mentioned is the product sold under the name Tipo Carbomagel by the company Buschle & Lepper (oil uptake equal to 2.14 ml/g).

The oil-absorbing fillers that are particularly preferred are silica and silica silylate powders and more particularly the products sold under the name Sunsphere® H33 by the company Asahi Glass and under the name Dow Coming VM-2270 Aerogel Fine Particles by the company Dow Corning; nylon-6 powder and porous polymethyl methacrylate (INCI name methyl methacrylate crosspolymer) such as the spheres sold under the name Covabead LH85 by the company Sensient.

In a particular embodiment, the filler having a oil absorption capacity greater or equal to 1 ml/g is an hydrophobic silica aerogel (silica silylate).

Silica aerogels are porous materials obtained by replacing (by drying) the liquid component of a silica gel with air.

They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles that may be used in the present invention have a specific surface area per unit of mass ($S_M$) ranging from 500 to 1500 $m^2$/g, preferably from 600 to 1200 $m^2$/g and better still from 600 to 800 $m^2$/g, and a size expressed as the mean volume diameter (D[0.5]), ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the hydrophobic silica aerogel particles that may be used in the present invention have a size expressed as the mean volume diameter (D[0.5]) ranging from 1 to 30 μm, preferably from 5 to 25 μm, better still from 5 to 20 μm and even better still from 5 to 15 μm.

The specific surface area per unit of mass may be determined via the BET (Brunauer-Emmett-Teller) nitrogen absorption method described in the *Journal of the American Chemical Society,* vol. 60, page 309, February 1938 and corresponding to the international standard ISO 5794/1 (appendix D). The BET specific surface area corresponds to the total specific surface area of the particles under consideration.

The size of the hydrophobic silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

According to one advantageous embodiment, the hydrophobic silica aerogel particles used in the present invention have a specific surface area per unit of mass ($S_M$) ranging from 600 to 800 m²/g and a size expressed as the mean volume diameter (D[0.5]) ranging from 5 to 20 μm and better still from 5 to 15 μm.

The hydrophobic silica aerogel particles used in the present invention may advantageously have a tamped density ρ ranging from 0.04 g/cm³ to 0.10 g/cm³ and preferably from 0.05 g/cm³ to 0.08 g/cm³.

In the context of the present invention, this density, known as the tamped density, may be assessed according to the following protocol:

40 g of powder are poured into a measuring cylinder; the measuring cylinder is then placed on a Stav 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in cm³ and m in g).

According to one embodiment, the hydrophobic silica aerogel particles that may be used in the present invention have a specific surface area per unit of volume $S_V$ ranging from 5 to 60 cm²/cm³, preferably from 10 to 50 m²/cm³ and better still from 15 to 40 m²/cm³.

The specific surface area per unit of volume is given by the relationship: $S_V = S_M \cdot \rho$; where ρ is the tamped density expressed in g/cm³ and $S_M$ is the specific surface area per unit of mass expressed in m²/g, as defined above.

Preferably, the hydrophobic silica aerogel particles according to the invention have an oil-absorbing capacity, measured at the wet point, ranging from 5 to 18 ml/g, preferably from 6 to 15 ml/g and better from 8 to 12 ml/g.

The oil-absorbing capacity measured at the wet point, noted Wp, corresponds to the amount of water that needs to be added to 100 g of particle in order to obtain a homogeneous paste.

It is measured according to the wet point method or the method for determining the oil uptake of a powder described in standard NF T30-022. It corresponds to the amount of oil adsorbed onto the available surface of the powder and/or absorbed by the powder by measuring the wet point, described below:

An amount m=2 g of powder is placed on a glass plate, and the oil (isononyl isononoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The hydrophobic silica aerogel particles that may be used according to the present invention are preferably of silylated silica type (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or siloxanes, so as to functionalize the OH groups with silyl groups Si-Rn, for example trimethylsilyl groups.

As regards the preparation of hydrophobic silica aerogels particles that have been surface-modified by silylation, reference may be made to document U.S. Pat. No. 7,470,725.

Use will be made in particular of hydrophobic silica aerogels particles surface-modified with trimethylsilyl groups with INCI name Silica silylate.

As hydrophobic silica aerogel particles that may be used in the invention, examples that may be mentioned include the aerogel sold under the name VM-2260 or VM-2270 (INCI name: Silica silylate), by the company Dow Corning, the particles of which have a mean size of about 1000 microns and a specific surface area per unit of mass ranging from 600 to 800 m²/g.

Mention may also be made of the aerogels sold by the company Cabot under the references Aerogel TLD 201, Aerogel OGD 201, Aerogel TLD 203, and ENOVA AEROGEL MT 1100.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 m²/g (oil uptake equal to 1080 ml/100 g).

Advantageously, the hollow particles in accordance with the invention are at least partly formed from hydrophobic silica aerogel particles, preferably those with a specific surface area per unit of mass ($S_M$) ranging from 500 to 1500 m²/g and preferably from 600 to 1200 m²/g, and a size expressed as the mean volume diameter (D[0.5]), ranging from 1 to 1500 μm, better still from 1 to 1000 μm, preferably to from 1 to 100 μm, in particular from 1 to 30 μm, more preferably from 5 to 25 μm, better still from 5 to 20 μm and even better still from 5 to 15 μm.

The use of the hollow particles according to the invention, in particular of hydrophobic silica aerogel particles, also advantageously makes it possible to improve the remanence of the cosmetic properties afforded by the composition on keratin materials, in particular the skin.

The filler(s) with an oil uptake of greater than or equal to 1 ml/g, preferably greater or equal than 1.5 ml/g may be present in a composition according to the invention in a content ranging from 0.1% to 20% by weight, preferably ranging from 0.5% to 15% by weight and preferentially ranging from 0.5% to 10% by weight relative to the total weight of the composition.

In particular for the hydrophobic silica aerogel particles, which are very efficient in term of oil absorption capacity, they may be present in an amount ranging from 0.1 to 5.0% by weight, preferably from 0.1 to 3.0% by weight, more preferably from 0.1 to 2.0% by total weight of the composition.

Physiologically Acceptable Medium

Besides the compounds indicated previously, a composition according to the invention comprises a physiologically acceptable medium.

The term "physiologically acceptable medium" is intended to denote a medium that is particularly suitable for applying a composition according to the invention to the skin.

The physiologically acceptable medium is generally adapted to the nature of the support onto which the composition is to be applied, and also to the form in which the composition is to be packaged.

A composition of the invention may be a dispersion or an emulsion.

A dispersion may be made : an aqueous phase or as an oily phase.

An emulsion may have an oily or aqueous continuous phase. Such an emulsion may be, for example, an inverse (W/O) emulsion or a direct (O/W) emulsion, or alternatively a multiple emulsion (W/O/W or O/W/O).

In the case of emulsions, inverse (W/O) emulsions are preferred.

Aqueous Phase

The composition according to the invention may comprise an aqueous phase.

The aqueous phase comprises water. A water that is suitable for use in the invention may be a floral water such as cornflower water and/or a mineral water such as Vittel water, Lucas water or La Roche Posay water and/or a spring water.

The aqueous phase may also comprise water-miscible organic solvents (at room temperature: 25° C.), for instance monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

The aqueous phase may also comprise stabilizers, for example sodium chloride, magnesium dichloride or magnesium sulfate.

The aqueous phase may also comprise any water-soluble or water-dispersible compound that is compatible with an aqueous phase, such as gelling agents, film-forming polymers, thickeners or surfactants, and mixtures thereof.

In particular, a composition of the invention may comprise an aqueous phase in a content ranging from 1% to 80% by weight, especially from 5% to 50% and more particularly from 10% to 45% by weight relative to the total weight of the composition.

According to another embodiment, a composition of the invention may be anhydrous.

An anhydrous composition may comprise less than 5% by weight of water relative to the total weight of the composition, in particular less than 3%, especially less than 2% and more particularly less than 1% by weight of water relative to the total weight of the composition.

More particularly, an anhydrous composition may be free of water.

Fatty Phase

A cosmetic composition in accordance with the present invention may comprise at least one liquid and/or solid fatty phase.

According to one embodiment, the composition according to the present invention is in the form of an emulsion.

In particular, a composition of the invention may comprise at least one liquid fatty phase, especially at least one oil as mentioned below.

The term "oil" means any fatty substance that is in liquid form at room temperature (20-25° C.) and at atmospheric pressure.

A composition of the invention may comprise a liquid fatty phase in a content ranging from 1% to 90%, in particular from 5% to 80%, in particular from 10% to 70% and more particularly from 20% to 50% by weight relative to the total weight of the composition.

The oily phase that is suitable for preparing the cosmetic compositions according to the invention may comprise hydrocarbon-based oils, silicone oils, fluoro oils or non-fluoro oils, or mixtures thereof.

The oils may be volatile or non-volatile.

They may be of animal, plant, mineral or synthetic origin.

The term "non-volatile oil" means an oil that remains on the skin or the keratin fibre, at room temperature and atmospheric pressure. More specifically, a non-volatile oil has an evaporation rate strictly less than 0.01 mg/cm$^2$/min.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

The term "volatile oil" means any non-aqueous medium that is capable of evaporating on contact with the skin or the lips in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits included.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

Volatile Oils

The volatile oils may be chosen from hydrocarbon-based oils containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, for instance the oils sold under the trade names Isopar® or Permethyl®.

Volatile oils that may also be used include volatile silicones, for instance volatile linear or cyclic silicone oils, especially those with a viscosity of less than or equal to 8 centistokes (cSt) ($8×10^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethylcyclopenta-siloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

According to one embodiment, a composition of the invention may comprise from 1% to 80% by weight, or even from 5% to 70% by weight, or even from 10% to 60% by weight and especially from 15% to 50% by weight of volatile oil relative to the total weight of the composition.

Non-Volatile Oils

The non-volatile oils may be chosen especially from non-volatile hydrocarbon-based, fluoro and/or silicone oils.

Non-volatile hydrocarbon-based oils that may especially be mentioned include:

- hydrocarbon-based oils of animal origin, such as perhydrosqualene,
- hydrocarbon-based oils of plant origin, such as phytostearyl esters, such as phytostearyl oleate, phytostearyl isostearate and lauroyl/octyldodecyliphytosteatyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, winter squash oil, millet oil, barley oil, quinoa oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, musk rose oil, sesame oil, soybean oil, sunflower oil, castor oil and watermelon seed oil, and mixtures thereof; or alternatively caprylic/capric acid triglycerides, such as those sold by the company Stearineries Dubois or those sold under the names Miglyol 810®, 812® and 818® by the company Dynamit Nobel,
- linear or branched hydrocarbons of mineral or synthetic origin, such as liquid paraffins and derivatives thereof petroleum jelly, polydecenes, polybutenes, hydrogenated polyisobutene such as Parleam, and squalane;
- synthetic ethers containing from 10 to 40 carbon atoms;
- synthetic esters, for instance the oils of formula $R_1COOR_2$, in which $R_1$ represents a linear or branched fatty acid residue containing from 1 to 40 carbon atoms and $R_2$ represents a hydrocarbon-based chain, which is especially branched, containing from 1 to 40 carbon atoms, on condition that the sum of the number of carbon atoms in the chains $R_1$ and $R_2$ is greater than or equal to 10. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate,
- polyol esters and pentaerythritol esters, for instance dipentaerythrityl tetrahydroxystearate/tetraisostearate,
- esters of diol dimers and of diacid dimers, such as Lusplan DD-DA5® and Lusplan DD-DA7® sold by the company Nippon Fine Chemical and described in patent application US 2004-175 338,
- copolymers of a dial dimer and of a diacid dimer and esters thereof, such as dilinoleyl diol dimer/dilinoleic dimer copolymers and esters thereof, for instance Plandool-G,
- copolymers of polyols and of diacid dimers, and esters thereof, such as Hailuscent ISDA or the dilinoleic acid/butanediol copolymer,
- fatty alcohols that are liquid at room temperature, with a branched and/or unsaturated carbon-based chain containing from 12 to 26 carbon atoms, for instance 2-actyldodecanol, isostearyl alcohol, oleyl alcohol, 2-hexyldecanol, 2-butyloctanol and 2-undecylpentadecanol;
- $C_{12}$-$C_{22}$ higher fatty acids, such as oleic acid, linoleic acid or linolenic acid, and mixtures thereof,
- dialkyl carbonates, the two alkyl chains possibly being identical or different, such as dicaprylyl carbonate sold under the name Cetiol CC® by Cognis,
- oils of high molar mass, in particular having a molar mass ranging from about 400 to about 10 000 g/mol, in particular from about 650 to about 10 000 g/mol, in particular from about 750 to about 7500 g/mol and more particularly ranging from about 1000 to about 5000 g/mol. As oils of high molar mass that may be used in the present invention, mention may especially be made of oils chosen from:
  lipophilic polymers,
  linear fatty acid esters with a total carbon number ranging from 35 to 70,
  hydroxylated esters,
  aromatic esters,
  $C_{24}$-$C_{28}$ branched fatty acid or fatty alcohol esters,
  silicone oils,
  oils of plant origin, and
  mixtures thereof;
- optionally partially hydrocarbon-based and/or silicone fluoro oils, for instance fluorosilicone oils, fluoropolyethers and fluorosilicones as described in document EP-A-847 752;
- silicone oils, for instance linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl dimethicones, phenyl dimethicones, phenyl trimethylsiloxy diphenyl siloxanes, to diphenyl dimethicones, diphenyl methyldiphenyl trisiloxanes and 2-phenylethyl trimethylsiloxy silicates, and mixtures thereof.

According to one particular embodiment, the fatty phase of the composition according to the invention can contain only volatile compounds.

Dyestuffs

A composition according to the invention may also comprise at least one dyestuff.

The amount of dyestuff(s) in the base or primer composition of the invention will generally range from 0 to 5% by weight of total weight of the composition, in particular from 0.5 to 3% by weight of total weight of the composition.

In a particular embodiment, the composition will contain a low amount of titanium dioxide, ie less than 5% by weight, preferably less than 3% by weight of titanium dioxide.

A cosmetic composition in accordance with the invention may incorporate at least one dyestuff chosen from mineral or organic pigments conventionally used in cosmetic compositions, liposoluble or water-soluble dyes, materials with a specific optical effect, and mixtures thereof.

The term "pigments" should be understood to mean white or coloured, inorganic or organic particles which are insoluble in an aqueous solution and are intended for colouring and/or opacifying the resulting film.

As inorganic pigments that can be used in the invention, mention may be made of titanium oxides, zirconium oxides or cerium oxides, and also zinc oxides, iron oxides or chromium oxides, ferric blue, manganese violet, ultramarine blue and chromium hydrate. According to one particular mode of the invention, the mineral pigments will be chosen from iron oxides and titanium oxides, and mixtures thereof.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The colorant may also comprise a pigment having a structure which may be, for example, of the type such as silica microspheres containing iron oxide. An example of a pigment having this structure is the product sold by the company Miyoshi under the reference PC Ball PC-LL-100 P, this pigment being constituted of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPP) described in documents EP 0 542 669, EP 0 787 730, EP 0 787 731 and WO 96/08537.

The cosmetic composition according to the invention may also comprise water-soluble or fat-soluble dyes. The liposoluble dyes are, for example, Sudan red, DC Red 17, DC Green 6, β-carotene, soybean oil, Sudan brown, DC Yellow 11, DC Violet 2, DC Orange 5 and quinoline yellow. The water-soluble dyes are, for example, beetroot juice and caramel.

Additional Fillers

A composition in accordance with the invention may also comprise at least one additional tiller, of organic or mineral nature, making it possible especially to give it additional matt-effect or covering properties, and/or improved stability with regard to exudation and migration-resistance properties after application.

The term "filler" should be understood to mean colourless or white solid particles of any shape which are in a than that is insoluble and dispersed in the medium of the composition. These particles, of mineral or organic nature, can give body or rigidity to the composition and/or softness and uniformity to the makeup.

The fillers used in the compositions according to the present invention may be in lamellar, globular or spherical form, in the form of fibres or in any other intermediate form between these defined forms.

The fillers according to the invention may or may not be surface-coated, and in particular they may be surface-treated with silicones, amino acids, fluoro derivatives or any other substance that promotes the dispersion and compatibility of the filler in the composition.

Examples of mineral fillers that may be mentioned include talc, mica, silica, kaolin, calcium carbonate, magnesium carbonate, hydroxyapatite, glass or ceramic microcapsules.

Examples of organic fillers that may be mentioned include polyethylene powder or polymethyl methacrylate powder, polytetrafluoroethylene (Teflon) powders, lauroyllysine, hexamethylene diisocyanate/trimethylol hexyl lactone copolymer powder (Plastic Powder from Toshiki), silicone resin microbeads (for example Tospearl from Toshiba), natural or synthetic micronized waxes, metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, and polyurethane powders, in particular crosslinked polyurethane powders comprising a copolymer, the said copolymer comprising trimethylol hexyl lactone. It may in particular be a hexamethylene diisocyanate/trimethylol hexyl lactone polymer. Such particles are especially commercially available, for example, under the name Plastic Powder D-400® or Plastic Powder D-800® from the company Toshiki, and mixtures thereof.

Additives

In a particular embodiment, a cosmetic composition according to the invention further comprises at least one compound chosen from water, hydrophilic solvents, lipophilic solvents, oils, and mixtures thereof.

A cosmetic composition according to the invention may also comprise any additive usually used in the field under consideration, chosen, for example, from gums, anionic, cationic, amphoteric or nonionic surfactants, silicone surfactants, resins, thickening agents, structuring agents such as waxes, dispersants, antioxidants, essential oils, preserving agents, fragrances, neutralizers, antiseptics, UV-screening agents, cosmetic active agents, such as vitamins, moisturizers, emollients or collagen-protecting agents, and mixtures thereof.

It is a matter of routine operations for a person skilled in the art to adjust the nature and amount of the additives present in the compositions in accordance with the invention such that the desired cosmetic properties and stability properties thereof are not thereby affected.

A cosmetic composition of the invention may be in the form of a skin makeup product, in particular a foundation, a hot-cast foundation product, a body makeup product, a concealer, an eyeshadow or a lipstick. It may be in the form of an anhydrous gel, in the form of a stick or wand, or in the form of a soft paste.

A care composition according to the invention may in particular be an antisun composition.

Preferably, the composition according to the invention is in the form of a fluid primer or a fluid foundation.

In a particular embodiment, the composition is an emulsion.

The invention also concerns a cosmetic process comprising a step of applying at least one layer of the cosmetic composition according to the invention, onto the skin, in particular the skin of the face.

In a particular embodiment, the cosmetic composition is applied alone or as a base or primer under a skin care product or a make up product.

The cosmetic process is particularly intended to decrease the visibility of skin imperfections, in particular the pores and make the pore hiding effect long lasting.

EXAMPLES

All compositions are written with percentages by weight. They were prepared according to the same protocol: mix oil phase ingredients together and heat up to 60-80° C. until wax is melted, disperse pigments and fillers inside the oil phase then proceed to emulsification by adding water phase ingredients.

Example 1: Effect of the Combination of Filler with RI>1.6, Silicon Elastomer and Filler Having Oil Absorption >1 ml/g on Pore Hiding and Long Lasting Compared to original formula F1, the following modifications were done:

silicon elastomer (DC9041) was replaced by dimethicone (Silicone Fluid 5CS) in formula F2 boron nitride (Sottouch) was replaced by a low refractive index plate type filler, talc (Luzenac 00) in formula F3 and by a large size plate type filler, $TiO_2$ coated mica pearl (Flamenco Blue) in formula F4 porous PMMA (Covabead) was replaced by non-porous PMMA (Micropearl M100) in formula F5

| INCI | F1 invention | F2 comparative | F3 comparative | F4 comparative | F5 comparative |
|---|---|---|---|---|---|
| Dimethicone (Silicone Fluid 2CS) | 22.00 | 22.00 | 22.00 | 22.00 | 22.00 |
| Dimethicone (Silicone Fluid 5CS) | — | 16.00 | — | — | — |
| Dimethicone - PEG/PPG-18/8 Dimethicone (X-22-6711D) | 2.00 | 2.00 | 2.00 | 2.00 | 2.00 |
| PEG-10 Dimethicone (KF-6017) | 1.00 | 1.00 | 1.00 | 1.00 | 1.00 |
| Dimethicone - Dimethicone crosspolymer (Dow Corning 9041) | 16.00 | — | 16.00 | 16.00 | 16.00 |
| Tribehenin (Syncrowax HR-C) | 1.00 | 1.00 | 1.00 | 1.00 | 1.00 |
| Ethylhexyl methoxycinnamate (Parsol MCX) | 5.00 | 5.00 | 5.00 | 5.00 | 5.00 |
| Iron oxides - Disodium stearoyl glutamate - Aluminium dioxide (NAI-C33-9001) | 0.22 | 0.22 | 0.22 | 0.22 | 0.22 |
| Iron oxides - Disodium stearoyl glutamate - Aluminium dioxide (NAI-C33-8001) | 0.06 | 0.06 | 0.06 | 0.06 | 0.06 |
| Titanium dioxide - Disodium stearoyl glutamate - Aluminium dioxide (NAI-TAO-77891) | 2.72 | 2.72 | 2.72 | 2.72 | 2.72 |
| Boron nitride (Softouch CC6058) | 3.00 | 3.00 | — | — | 3.00 |
| Talc (Luzenac 00) | — | — | 3.00 | — | — |
| Mica - Titanium dioxide (Flamenco Blue 620C) | — | — | — | 3.00 | — |
| Methyl methacrylate crosspolymer (Covabead LH85) | 2.00 | 2.00 | 2.00 | 2.00 | — |
| Polymethyl methacrylate (Micropearl M100) | — | — | — | — | 2.00 |
| Magnesium sulfate | 1.00 | 1.00 | 1.00 | 1.00 | 1.00 |
| Phenoxyethanol | 0.50 | 0.50 | 0.50 | 0.50 | 0.50 |
| Caprylyl glycol | 0.50 | 0.50 | 0.50 | 0.50 | 0.50 |
| Butylene glycol | 2.00 | 2.00 | 2.00 | 2.00 | 2.00 |
| Glycerin | 3.00 | 3.00 | 3.00 | 3.00 | 3.00 |
| Water | 34.00 | 34.00 | 34.00 | 34.00 | 34.00 |
| Alcohol | 4.00 | 4.00 | 4.00 | 4.00 | 4.00 |
| TOTAL | 100 | 100 | 100 | 100 | 100 |

Refractive indexes of boron nitride (Softouch) and talc (Luzenac 00) are respectively about 1.65 and 1.58 (<1.6).

Average particle sizes of boron nitride (Softouch) and TiO2 coated mica (Flamenco Blue 620C) are respectively about 11 μm and 22 μm (>20 μm).

Oil absorption capacities of porous PMMA (Covabead) and non-porous PMMA (Micropearl M100) are respectively about 1.2 ml/g and 0.5 ml/g (<1 ml/g).

The formulas where tested in an expert evaluation wherein the following criteria were evaluated: pore hiding, skin brightening, color homogeneity, long lasting. The test consists in the application of 0.1 g of product on half face of 6 different panelists to see the differences between two formulas The results are presented in the table hereunder:
+++: very high effect
++: high effect
+/−: low effect
−: no effect

TABLE 1

Results

| Attribute | F1 (invention) | F2 (comparative) | F3 (comparative) | F4 (comparative) | F5 comparative |
|---|---|---|---|---|---|
| Pore hiding | +++ | − | +/− | − | ++ |
| Skin brightening | ++ | ++ | +/− | ++ | ++ |
| Color homogeneity | +++ | +/− | ++ | − | +/− |
| Long lasting | ++ | − | − | − | +/− |

The formula F1 shows better pore hiding effect than formulas F2, F3, F4 and F5. Moreover, lasting of pore hiding effect is better for formula F1 than for formula F5. As a result, the association of plate type filler with high refractive index (>1.6), silicon elastomer and filler with strong oil absorption capacity (>1 ml/1 g) is able to decrease the visibility of pores and to keep this effect during the day.

Example 2: Make-Up Base Formulas

Here are other examples of makeup base formulas with good properties in term of pore hiding effect, skin brightening, color homogeneity and long lasting, including similar fillers association.

| INCI | F6 | F7 |
|---|---|---|
| Dimethicone (Silicone Fluid 2CS) | 23.00 | 23.00 |
| Dimethicone - PEG/PPG-18/8 Dimethicone (X-22-6711D) | 2.00 | 2.00 |
| PEG-10 Dimethicone (KF-6017) | 1.00 | 1.00 |
| Dimethicone - Dimethicone crosspolymer (Dow Corning 9041) | 12.00 | 12.00 |
| Tribehenin (Syncrowax HR-C) | 1.00 | 1.00 |
| Ethylhexyl methoxycinnamate (Parsol MCX) | 6.00 | 6.00 |
| Iron oxides - Disodium stearoyl glutamate - Aluminium dioxide (NAI-C33-9001) | 0.11 | 0.11 |
| Iron oxides - Disodium stearoyl glutamate - Aluminium dioxide (NAI-C33-8001) | 0.05 | 0.05 |
| Titanium dioxide - Disodium stearoyl glutamate - Aluminium dioxide (NAI-TAO-77891) | 2.34 | 2.34 |
| Boron nitride (Softouch CC6058) | 3.00 | — |
| Boron nitride (PUHP 1030L) | — | 3.00 |
| Vinyl dimethicone/Methicone silsesquioxane (KSP100) | 4.00 | 4.00 |
| Methyl methacrylate crosspolymer (Covabead LH85) | 2.00 | 2.00 |
| Silica silylate (VM-2270 Aerogel) | 0.50 | 0.50 |
| Magnesium sulfate | 0.70 | 0.70 |
| Phenoxyethanol | 0.50 | 0.50 |
| Caprylyl glycol | 0.50 | 0.50 |
| Butylene glycol | 2.00 | 2.00 |
| Glycerin | 3.00 | 3.00 |
| Water | 32.30 | 32.30 |
| Alcohol | 4.00 | 4.00 |
| TOTAL | 100 | 100 |

Sensorial Evaluation

After application on the skin, the formulas makes the pores less visible and keep the covering pores during the day. It spread smoothly, the texture was soft and did not make the skin feel and look dry during the day, nor the skin have oily shine badly.

Effect as a Make-Up Base or Primer Wider a Foundation

F6 formula was also found to improve lasting of overall makeup result and especially mat effect when it was applied as a base layer before foundation. Instrumental evaluation of mat effect with polarimetric camera was performed on 8 different panelists after application of 'TWC' (Two Way Cake) foundation only or above mentioned makeup base (MUB) and foundation (0.1 g on half face for each). After 3 h, mat effect was better when makeup base was applied before foundation.

TABLE 2

Polarimetric camera data

| Product | Mat (Timm-T0) | Mat (T3 h-T0) | Mat (T3 h-Timm) |
|---|---|---|---|
| F8 | −8.59 ± 2.96 | 0.73 ± 5.82 | 9.32 ± 4.44 |
| F6 + F8 | 44.43 ± 3.49 | −9.02 ± 4.09 | 5.41 ± 1.96 |

TWC foundation formula used in instrumental test

| INCI | F8 |
|---|---|
| Talc - Dimethicone (SA-13R) | 42.47 |
| Mica (Sericite SL) | 18.00 |
| Nylon-12 | 6.00 |
| Vinyl dimethicone/Methicone silsesquioxane (KSP100) | 6.00 |
| Titanium dioxide | 14.00 |
| Iron oxides | 2.83 |
| Caprylic/Capric triglyceride | 2.00 |

TABLE 2-continued

| Polarimetric camera data | |
| --- | --- |
| Dimethicone (KF-96A) | 5.30 |
| Ethylhexyl methoxycinnamate (Parsol MCX) | 3.00 |
| Preservatives | 0.40 |
| TOTAL | 100 |

Application of a make-up base according to the invention makes the overall look with other makeup product last longer and beautify the look after other face makeup. It is easy for next-step face makeup to apply smoothly and evenly whiten skin tone.

The invention claimed is:

1. A cosmetic process for decreasing the visibility of skin imperfections, comprising a step of applying at least one layer of a cosmetic composition to skin, wherein said cosmetic composition comprises in a physiological medium:
   (i) at least one plate type boron nitride filler having a refractive index between about 1.6 and about 2.2 and having a particle size ranging from about 1 μm to about 20 μm, wherein the total amount of boron nitride present in the composition ranges from about 2% to about 5% by weight, relative to the total weight of the composition,
   (ii) at least one non-emulsifying silicon elastomer, wherein the total amount of non-emulsifying silicone elastomer particle present in the composition ranges from about 3% to about 30% by weight, relative to the total weight of the composition, and
   (iii) at least one filler having an oil absorption capacity greater than or equal to 1 ml/g chosen from hydrophobic silica aerogel particles, wherein the at least one filler having oil absorption capacity greater than or equal to about 1 mL/g is present in an amount ranging from about 0.1% to about 2% by weight, relative to the total weight of the composition.

2. The cosmetic process of claim 1, wherein the cosmetic composition comprises from 0 to 5% of dyestuffs by total weight of the composition.

3. The cosmetic process of claim 1, wherein the at least one non-emulsifying silicon elastomer is in the form of a gel or a powder.

4. The cosmetic process of claim 1, wherein the at least one filler having an oil absorption capacity greater than or equal to 1 ml/g is chosen from hydrophobic silica aerogel particles having a specific surface area per unit of mass ($S_M$) ranging from 500 to 1500 m$^2$/g, and a size expressed as the mean volume diameter (D[0.5]) ranging from 1 to 1500 μm.

5. The cosmetic process of claim 1, wherein the at least one filler having an oil absorption capacity greater than or equal to 1 ml/g is chosen from hydrophobic silica aerogel particles having an oil-absorbing capacity, measured at the wet point, ranging from 5 to 18 ml/g.

6. The cosmetic process of claim 1, wherein the at least one filler having an oil absorption capacity greater than or equal to 1 ml/g is chosen from hydrophobic silica aerogel particles having tamped density ρ ranging from 0.04 g/cm$^3$ to 0.10 g/cm$^3$.

7. The cosmetic process according to claim 1, wherein the at least one filler having an oil absorption capacity greater than or equal to about 1 mL/g is chosen from hydrophobic silica aerogel particles that are surface modified by at least one trimethylsilyl group.

8. The cosmetic process of claim 1, wherein the cosmetic composition is an emulsion.

9. The cosmetic process of claim 1, wherein the cosmetic composition is a liquid.

10. The cosmetic process according to claim 1, further comprising at least one additional component chosen from water, hydrophilic solvents, lipophilic solvents, oils, or mixtures thereof.

11. The cosmetic process according to claim 1, wherein the cosmetic composition is in the form of a base, primer, skin care base, skin care primer, make-up base, or make-up primer.

12. The cosmetic process of claim 1, wherein the cosmetic composition is applied to facial skin.

13. The cosmetic process according to claim 1, wherein the cosmetic composition is applied as a base or primer under a skin care product or a make-up product.

14. The cosmetic process of claim 1, wherein the at least one filler having an oil absorption capacity greater than or equal to 1 ml/g is chosen from hydrophobic silica aerogel particles having tamped density ρ ranging from 0.05 g/cm$^3$ to 0.08 g/cm$^3$.

* * * * *